United States Patent
Bellin et al.

(10) Patent No.: US 7,105,116 B2
(45) Date of Patent: Sep. 12, 2006

(54) NON-ROTATING BREAST IMPLANT (75) Inventors: Howard T. Bellin, 105 E. 73rd St., New York, NY (US) 10021; Kenneth C. Kredovski, Roseville, MN (US); Ruairidh W. Campbell, Salt Lake City, UT (US)

(73) Assignee: Howard T. Bellin, New York, NY (US)

( * ) Notice: Subject to any disclaimer, the term of this patent is extended or adjusted under 35 U.S.C. 154(b) by 0 days.

(21) Appl. No.: 10/462,278

(22) Filed: Jun. 16, 2003

(65) Prior Publication Data
US 2003/0205846 A1 Nov. 6, 2003

Related U.S. Application Data (62) Division of application No. 09/452,656, filed on Dec. 1, 1999, now Pat. No. 6,692,527.

(51) Int. Cl.
*B29C 35/02* (2006.01)
*B29C 41/14* (2006.01)

(52) U.S. Cl. ............... 264/131; 264/236; 264/254; 264/255; 264/305; 264/308

(58) Field of Classification Search ............ 623/8; 264/299, 301, 302, 303, 305, 306, 307, 308, 264/250, 254, 255, 256, 131, 135, 236, 347; 427/2.24
See application file for complete search history.

(56) References Cited

U.S. PATENT DOCUMENTS

| | | | |
|---|---|---|---|
| 2,747,229 A * | 5/1956 | Teague ............... 264/257 |
| 3,293,663 A | 12/1966 | Cronin | |
| 3,600,718 A | 8/1971 | Boone | |
| 3,681,787 A | 8/1972 | Perras | |
| 3,852,832 A | 12/1974 | McGhan et al. | |
| 4,298,997 A | 11/1981 | Rybka | |
| 4,364,880 A * | 12/1982 | Howse ............... 264/28 |
| 4,472,226 A * | 9/1984 | Redinger et al. ........ 156/242 |
| 4,889,744 A * | 12/1989 | Quaid ............... 427/2.24 |
| 4,950,292 A | 8/1990 | Audretsch | |
| 4,955,909 A | 9/1990 | Ersek et al. | |
| 4,960,425 A * | 10/1990 | Yan et al. ............ 623/8 |
| 5,022,942 A | 6/1991 | Yan et al. | |
| 5,026,394 A * | 6/1991 | Baker ............... 623/8 |

(Continued)

OTHER PUBLICATIONS

Dow Corning, Silastic Mammary Prosthesis: Round Design, Bulletin dated Oct. 1974, six pages, Dow Corning Corporation, Midland, Michigan, U.S.A.

*Primary Examiner*—Angela Ortiz (57) ABSTRACT

A non-rotating anatomical-shaped breast implant having a front side with a smooth surface and a rear side with a textured surface. A smooth surface ripples or wrinkles little, if at all. Rippling or wrinkling of the implant may undesirably produce a visible or palpable waviness on the skin of the breast. A smooth surface is more likely to produce the look and feel of a natural breast. A rear side with a textured surface is desirable because tissue growth of the body, after the implant has been implanted, engages the textured surface to anchor the implant in place such that the front side with the smooth surface remains matched with the front side of the body and such that the anatomical-shaped breast implant with its tear drop shaped fullness remains at a natural position within the breast. The disclosure further includes a method for minimizing the rotation of an implant within the body and a method for making an implant envelope that has different thicknesses.

9 Claims, 13 Drawing Sheets

U.S. PATENT DOCUMENTS

| | | | |
|---|---|---|---|
| 5,354,338 A | * | 10/1994 | Ledergerber .................... 623/8 |
| 5,522,896 A | * | 6/1996 | Prescott ................... 623/23.56 |
| 5,525,275 A | * | 6/1996 | Iversen et al. ................ 264/28 |
| 5,545,220 A | * | 8/1996 | Andrews et al. ............... 623/8 |
| 5,630,844 A | | 5/1997 | Dogan et al. |
| 5,662,708 A | | 9/1997 | Hayes et al. |
| 5,674,285 A | | 10/1997 | Quaid |
| 6,783,793 B1 | * | 8/2004 | Hossainy et al. .......... 427/2.25 |

* cited by examiner

NON-ROTATING BREAST IMPLANT

This application is a divisional of application Ser. No. 09/452,656 filed on Dec. 1, 1999, now U.S. Pat. No. 6,692,527.

BACKGROUND OF THE INVENTION

The present invention relates generally to implants for the body and particularly to implants that have features that minimize or prevent rotation of an implant in a body. More specifically, the present invention is a breast implant that has an anatomical shape that gives a more natural look to the augmented breast, but cannot rotate because it has a texturing on the back that anchors it, yet is smooth on the surface to minimize rippling.

The preferred shape for an implant used for cosmetic breast augmentation is the so-called "anatomical shape" that is also referred to as "tear drop." This shape has more of the substance filling the silicone elastomer shell in the inferior pole of the implant and less in the superior pole, thus mimicking the natural shape of the breast. For a given volume, round shaped implants have too much substance in the upper pole that can make the breast look artificial. The anatomical implant looks much more natural.

A problem with anatomical implants is that if the outer surface of the implant is smooth, the implant can rotate. When an implant is surgically placed beneath the breast or beneath the chest muscle, the body recognizes that it is a foreign object and walls it off with tissue that is referred to as a "capsule." A smooth-walled implant creates a smooth capsule that can allow the implant to slip and slide within it. When a smooth-walled anatomical-shaped breast implant rotates, as it often does, there is more fullness laterally or medially instead of inferiorally as intended. This creates an unacceptable deformity. Thus far the only solution to this problem has been the use of "textured" implants which have a rough surface. They produce a capsule that is reciprocally rough. The "male-female" relationship of the implant and capsule holds the implant in place and prevents its rotation.

Textured implants have a very distinct disadvantage, however. The problem is that textured implants have a tendency to ripple (i.e. produce a folding, wrinkling or waviness on the surface of the implant). Rippling creates an extremely unsatisfactory appearance. Causes of or factors contributing to rippling may be 1) that textured implants are cured twice, while smooth walled implants are cured once, 2) that the textured implant is formed with an additional coating of the silicone elastomer, leading to a thicker wall that is less able to support itself and thus may fold, and/or 3) the texture itself (peaks and valleys in the surface of the implant) may produce a variety of non-linear scores or fold lines along which the wall of the implant folds or ripples.

Rippling—visible or palpable waviness on the implant surface—is one of the major problems with breast implants. This folding of the implant can often be felt or seen and can be extremely obtrusive. Therefore, to solve the problem of implant rotation with texturing the entire implant as is presently done, one must compound the problem of severe, unacceptable rippling.

The present invention provides a solution to the problem. The present invention is an implant that is textured on its posterior surface, but smooth on its anterior surface. The textured posterior surface causes a reciprocal textured capsule, but only behind the implant. This interlocking with the capsule keeps the implant from rotating. However, the textured area is only on the back of the implant; therefore, any rippling will not be visible or palpable. The anterior surface will remain smooth—and minimize any unsatisfactory rippling.

Preferred fill materials for the non-rotating anatomical-shaped breast implant include saline and viscous fill materials. Among viscous fill materials, silicone gel, soy oil, and hydrogels are preferred, with hydrogels being most preferred.

SUMMARY OF THE INVENTION

A feature of the present invention is a non-rotating breast implant.

Another feature of the present invention is a non-rotating anatomical-shaped breast implant.

Another feature of the present invention is an implant having a first surface portion that engages tissue in the body to anchor with little or no rotation the implant in the body and a second surface portion that has a desirable characteristic when oriented in a particular direction.

Another feature of the present invention is an implant having a textured surface portion that engages tissue growth in the body so as to anchor with little or no rotation the implant in the body and a second surface portion that is smooth.

Another feature of the present invention is a non-rotating anatomical-shaped breast implant with a posterior surface and an anterior surface where the posterior surface comprises a texture to anchor the implant in the body and where the anterior surface comprises a smooth face to minimize wrinkling.

Another feature of the present invention is a non-rotating breast implant having a first side with a relatively rough surface or surface portion to interlock with body tissue to anchor the implant and having a second side with a relatively smooth surface or surface portion that forms little or no wrinkles and that therefore may be oriented close to the skin to provide a natural appearance.

Another feature of the present invention is a method for minimizing or preventing rotation of an implant in a body so as to permanently fix the orientation of a desirable characteristic of the implant.

Another feature of the present invention is a method for minimizing or preventing rotation in a body of an anatomical-shaped implant so as to permanently fix the anterior orientation of the front side of the anatomical-shaped implant.

Another feature of the present invention is a method of making an envelope for an implant, where the method includes the separate steps of 1) fully submerging and 2) partially submerging a mandrel in a dispersion. The steps may occur in any sequence and be repeated.

The method includes selecting, preferably, an anatomical-shaped mandrel. Then the mandrel is dipped four times in a dispersion of a silicone elastomer and solvent (such as xylene). After each of the dips, the solvent is permitted to evaporate or partially evaporate so as to permit the just-coated layer to at least partially stabilize. After the fourth layer of silicone elastomer (or other envelope forming material) has stabilized, the envelope (still on the mandrel) is cured. The cured envelope, still on the mandrel, is then partially dipped into the dispersion, i.e., partially submerged to the level or over the portion of the envelope to which the texturing is to be applied. This layer (over a portion of the envelope) is then permitted to stabilize (but is not fully dried). Then granulated solid particles, such as salt particles (sodium chloride for example), are applied over (such as by being sprayed) the portion of the envelope that has the extra layer of now stabilized but not fully dried silicone elastomer. This portion of the envelope is the portion that is not perceptible (visibly or by touch) when the implant is implanted into the body. Preferably, such portion of the implant is the posterior side of the implant. Then the envelope is cured (vulcanized). After being cured, the envelope (still on the mandrel) is soaked in a solvent (such as water) to dissolve or wash off the solid granules, thereby leaving the textured surface. The envelope is then removed from the mandrel, patched and fitted with a valve for the fill material.

Another feature of the present invention is a breast implant having a first thickness at the nipple position and a second thickness on the posterior side.

An advantage of the present invention is that anatomical-shaped breast implants are held in position, with their superior poles correctly oriented in the superior position without slippage or spin off in the medial or lateral directions.

Another advantage of the present invention is that the anterior side of the breast implant takes on a more natural appearance and feel. Since the implant is anchored in place by tissue engaging the textured posterior side of the implant, the anterior side of the implant need not be textured and therefore may be made of a thinner envelope wall having a smooth surface. Thinner, smooth, once-cured envelope walls have less of a tendency to wrinkle or ripple than do thicker, textured, twice-cured walls. A wrinkle or ripple may be seen and/or felt through the skin of the natural breast.

DETAILED DESCRIPTION OF THE PREFERRED EMBODIMENTS

As shown in FIGS. 1A–D and 3A, an anatomical-shaped breast implant is designated in general by reference number 10. The implant 10 includes an envelope 12 and fill material 14 sealed in the envelope 12. The envelope 12 further includes a posterior (rear) side or face 16 that includes a textured or relatively rough surface 18 and an anterior (front) side or face 20 that is smooth or relatively smooth compared to the relatively rough surface 18. The envelope 12 further includes a right side 22 (shown in FIG. 1C) and a left side 24 (shown in FIG. 1D). Depending upon the breast into which the implant 10 is implanted, the right side 22 may be the medial or lateral side of the implant 10 and the left side 24 may be the medial or lateral side of the implant 10. The implant 10 further includes a superior (upper) pole 26 and an inferior (lower) pole 28. The anterior (front) side 20 of the envelope 12 has a smooth surface 30, relatively thin wall 32 and is cured once (though subject twice to curing temperatures). Most (over about 90%) of the right side 22 of the envelope 12 and most (over about 90%) of the left side 24 of the envelope 12 has a smooth surface 30 and a relatively thin wall portion 32 that is cured once (though is subject twice to curing temperatures). Further, the smooth surface 30 and the relatively thin wall portion 32 extend about a portion of each of the superior (upper) pole 26 and inferior (lower) pole 28. The posterior (rear) side 16 is formed by a relatively thick wall 34 of the envelope 12 that is textured and that is cured twice.

While it is preferable that an anatomical-shaped breast implant includes the features of the present invention, it should be noted that the features of the present invention may be used in an alternate embodiment of the invention, specifically a round shaped implant 36 shown in FIGS. 2A–D and 3B. The reference numbers of the anatomical-shaped implant 10 are noted on the round shaped implant 36 as prime reference numbers. In other words, the round shaped implant 36 includes an envelope 12' and fill material 14' sealed in the envelope 12'. The envelope 12' further includes a posterior (rear) side or face 16' that includes a textured surface 18' and an anterior (front) side or face 20' that is smooth. The envelope 12' further includes a right side 22' (shown in FIG. 2C) and a left side 24' (shown in FIG. 2D). Depending upon the breast into which the implant 36 is implanted, the right side 22' may be the medial or lateral side of the implant 36 and the left side 24' may be the medial or lateral side of the implant 36. The implant 36 further includes a superior (upper) pole 26' and an inferior (lower) pole 28'. The anterior (front) side 20' of the envelope 12' has a smooth surface 30', relatively thin wall 32' and is cured once (though subject twice to curing temperatures). One-half of the right side 22' of the envelope 12' and one-half of the left side 24' of the envelope 12' has a smooth surface 30' and a relatively thin wall portion 32' that is cured once (though subject twice to curing temperatures). Further, the smooth surface 30' and the relatively thin wall portion 32' extend about a portion of each of the superior (upper) pole 26' and inferior (lower) pole 28'. The posterior (rear) side 16' is formed by a relatively thick wall 34' of the envelope 12' that is textured and cured twice. As further shown in FIGS. 2A–D and unlike with the anatomical-shaped implant 10 of FIGS. 1A–D, one-half of the right side 22' has the textured surface 18' and one-half of the left side 24' has the textured surface 18'. Further, one-half of the surface about each of the poles 26' and 28' is the textured surface 18' and the other one-half of the pole surface is the smooth surface 30.

The envelope 12 is preferably formed of a material that is biocompatible, flexible, resilient and is substantially impermeable to the transport of water vapor. Rubber, such as a silicone elastomer, is a preferred material. The envelope 12 may also include a polymeric or copolymeric water vapor barrier layer that is extremely impermeable to the transport of water vapor and that has greater water vapor impermeability than a rubber such as a silicone elastomer. As to extremely impermeable water vapor barrier layers for implants, the following U.S. Patent is hereby incorporated by reference in its entirety: U.S. Pat. No. 5,630,844 issued May 20, 1997 and entitled Biocompatible Hydrophobic Laminate With Thermoplastic Elastomer Layer.

The present breast envelope is formed by dipping a mandrel into a silicone rubber dispersion. A dispersion may contain a silicone elastomer and a solvent (such as xylene). The mandrel is completely submerged and then raised out of the dispersion with a thin coating of the dispersion adhering to the mandrel. It should be noted that the first layer (formed by the first dip) is relatively thin since the dispersion flows readily off the smooth surface of the mandrel. The solvent is then caused to evaporate, such as with heat and/or by having air blown over the drying mandrels, and then the same mandrel having a layer of partially dried or at least partially stabilized silicone elastomer is dipped again (and allowed to at least partially stabilize) and again (and allowed to at least partially stabilize) until the desired thickness is obtained. In other words, after each of the first three dips, the envelope is ready to be dipped again when the partially stabilized just-coated layer has a certain tackiness, i.e. may leave a clear definition of a fingerprint without the finger picking up much if any of the dispersion (about 15 minutes after being dipped). After the fourth dip, the envelope of four layers is cured (still on the mandrel) at about 270° F. for about 90 minutes. Then the cured envelope of four layers is cooled to room temperature and inspected for waviness, bubbles and foreign material. The thickness of the final cured envelope is about $12/1000$ (0.012) inches thick to about $16/1000$ (0.016) inches thick.

As to making a breast envelope, the following U.S. Patents are hereby incorporated by reference in their entireties: U.S. Pat. No. 5,674,285 issued Oct. 7, 1997 and entitled Mammary Implant Having Shell With Unitary Rough-Textured Outer Layer and U.S. Pat. No. 5,630,844 issued May 20, 1997 and entitled Biocompatible Hydrophobic Laminate With Thermoplastic Elastomer Layer.

Figure 4A:
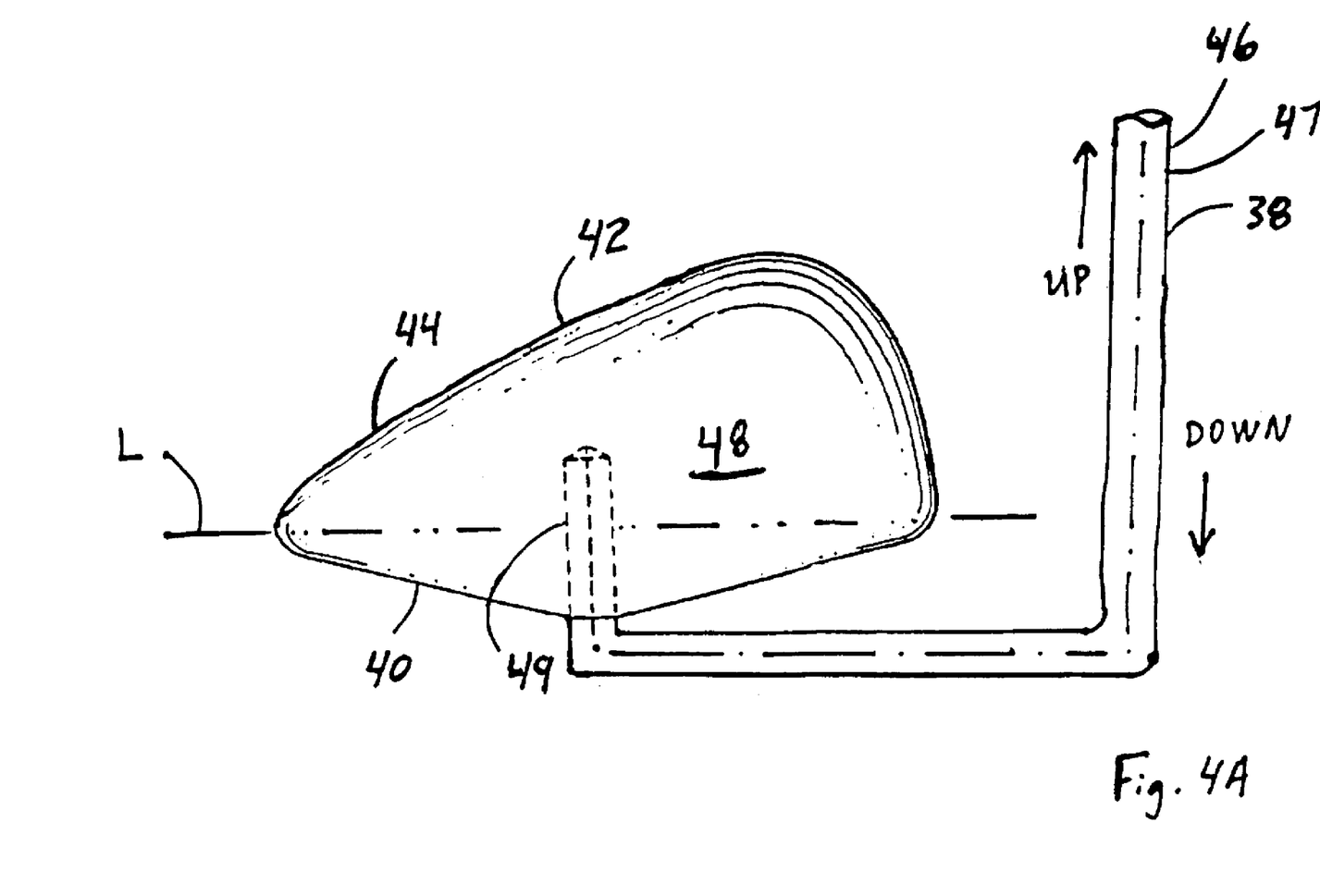
FIG. 4A shows a side view of a mandrel for the anatomical-shaped implant of FIG. 6A, and further shows a dipping rod engagable with the rear side of the mandrel.
Figure 4B:
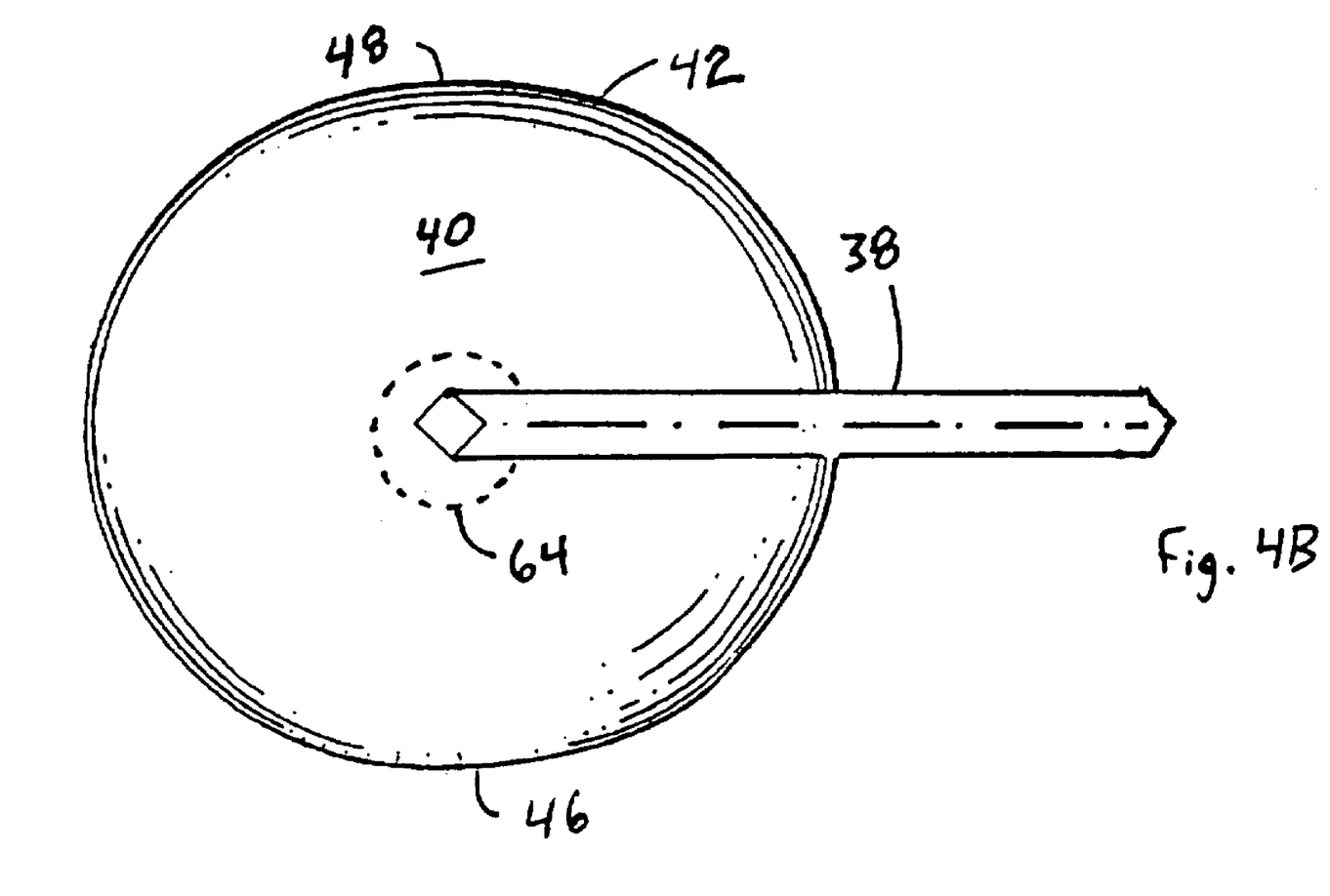
FIG. 4B shows a bottom view of the mandrel and dipping rod of FIG. 4A.
Figure 6A:
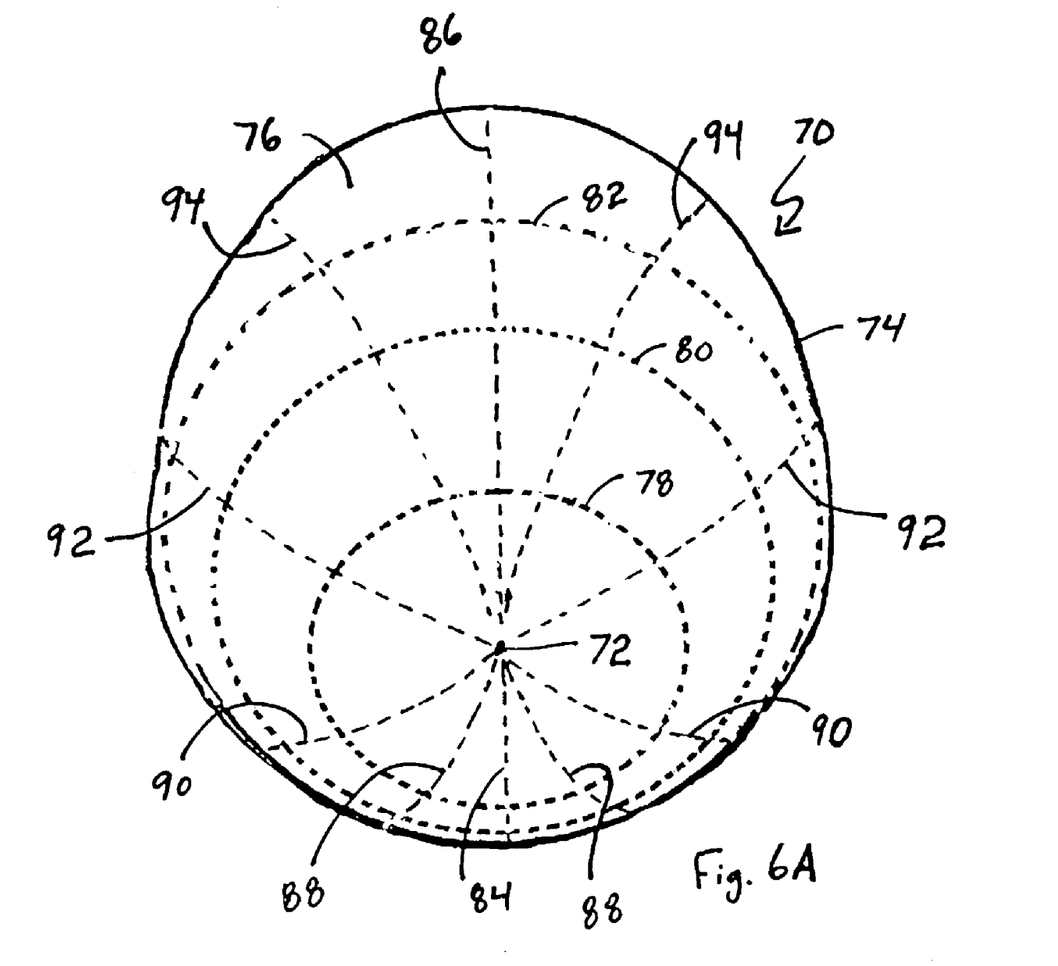
FIG. 6A shows a front or anterior view of an anatomical-shaped breast implant formed using the mandrel of FIGS. 4A and 4B.

As to making the envelope of the present invention with a relatively thin wall (such as thin wall 32) and a relatively thick wall (such as thick wall 34), please see FIGS. 4A and 4B. Here a generally U-shaped dipping rod 38 extends into the posterior side 40 of a mandrel 42. Mandrel 42 includes an anterior side 44. Mandrel 42 may be used to make the anatomical-shaped implant 70 of FIG. 6A. U-shaped dipping rod 38 includes a proximal end 47 (that may engage a handle for being manually dipped or that may engage an automatic dipping apparatus) and a distal end 49 that runs into the mandrel 42. Dipping rod 38 has a cross section that is square or diamond-shaped and runs into a square or diamond-shaped hole in the posterior side 40 of the mandrel 42 to minimize unintended spinning of the mandrel 42 relative to the dipping rod 38. With the U-shaped dipping rod 38, the posterior side 40 only of the mandrel 42 is dipped to level L into the dispersion (of a silicone elastomer and solvent) to the exclusion of anterior side 44 of the mandrel 42, further to the exclusion of over about 75% of a right side 46 (i.e. lateral or medial side depending upon the breast into which the implant is implanted) and further to the exclusion of over about 75% of a left side 48 (i.e. lateral or medial side depending upon the breast into which the implant is implanted) of the mandrel 42. Such a partial dip may be the first dip in a dipping process to form an envelope of the present invention, such as envelope 12. Preferably, such a partial dip is the last dip in the dipping process. Still further if desired, such a partial dip may be one of the "in-between" dips. Also, such a partial dip may not be limited to one partial dip. There may be two or more of such partial dips where only the posterior side 40 is dipped into the dispersion. After each partial dip or after each full dip, the solvent is permitted to evaporate and the mandrel 42 is again dipped into the dispersion until the anterior wall (such as wall 32) is the desired thickness and the posterior wall (such as wall 34) is the desired thickness.

Figure 5A:
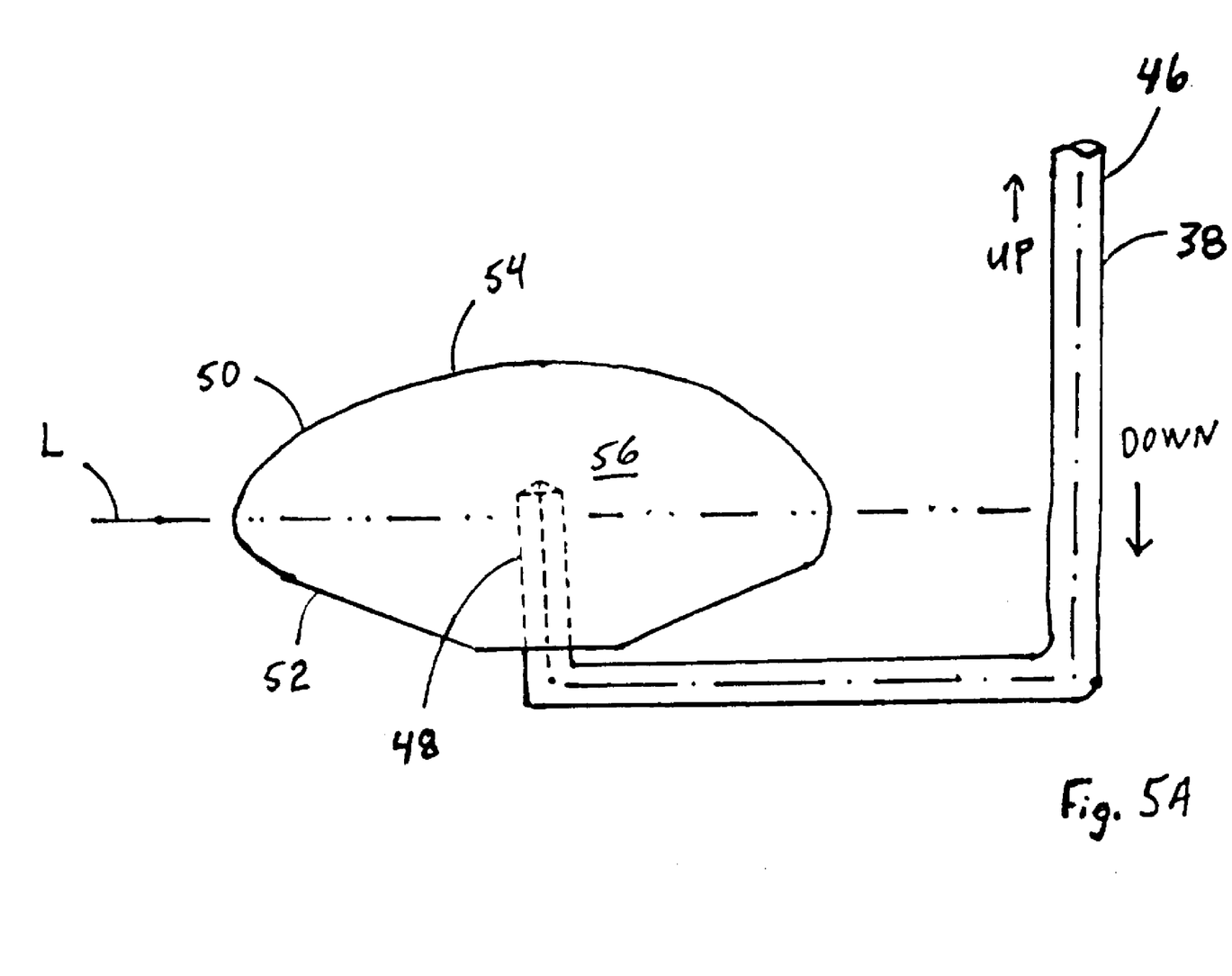
FIG. 5A shows a side view of a mandrel for the round shaped implant of FIGS. 2A–D.
Figure 5B:
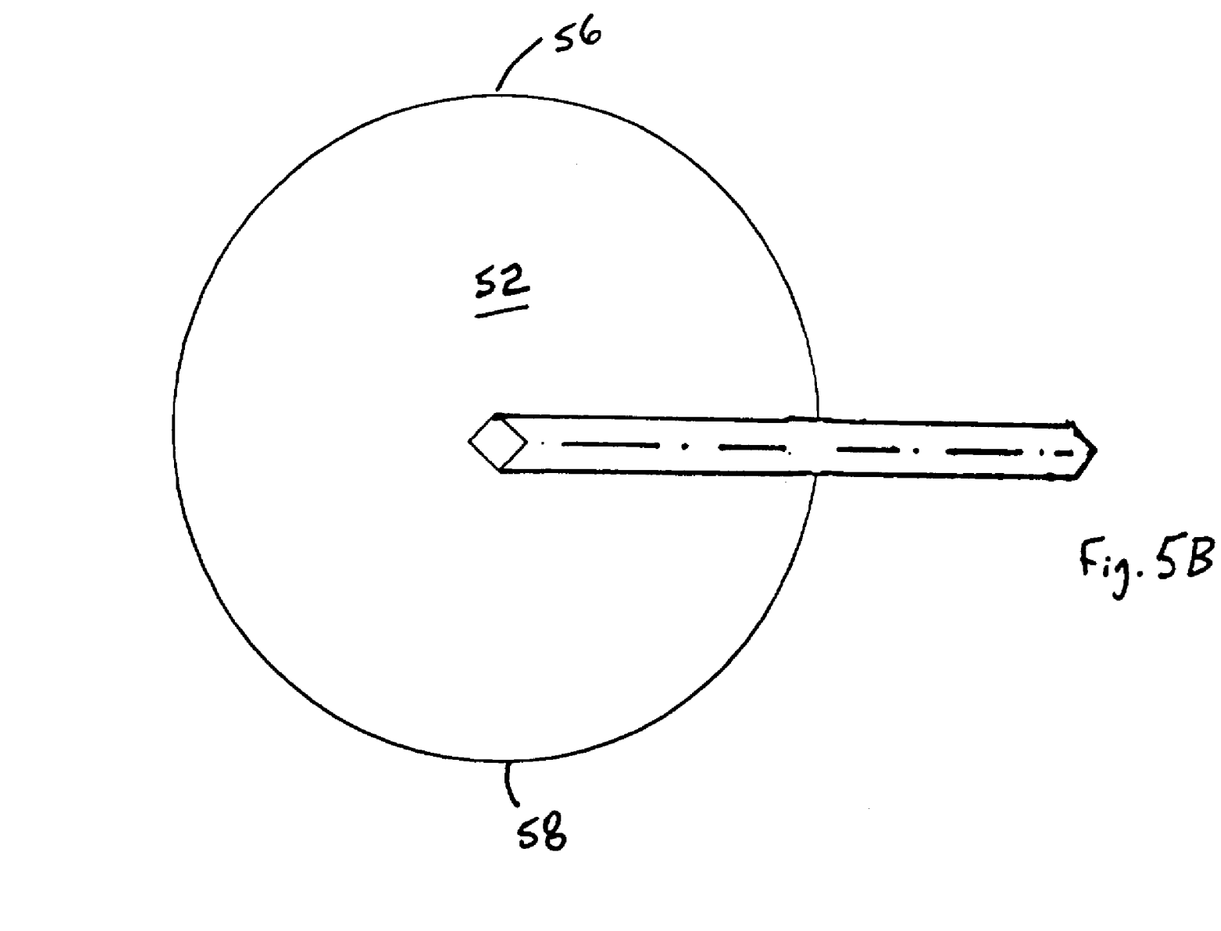
FIG. 5B shows a bottom view of the mandrel of FIG. 5A.

Envelope 12' is formed in an identical manner, except that the mandrel 50 of FIG. 5A is used. Mandrel 50 produces the round shaped implant 36 of FIGS. 2A–D. Mandrel 50 includes a posterior side 52, an anterior side 54, a right side 56 (i.e. lateral or medial side depending upon the breast into which the implant is implanted), and a left side 58 (i.e. lateral or medial side depending upon the breast into which the implant is implanted) corresponding to the posterior side 16', anterior side 20', right side 22', and left side 24' of implant 36. Mandrel 50 is fully submerged four times, then cured, then partially submerged to level L to form the posterior wall, then the posterior wall is sprayed with granulate sodium chloride, and then the envelope is cured and soaked in water to rid the envelope of the sodium chloride and expose the textured surface on the posterior wall.

Preferably, as to making the envelope 12 with a relatively thin wall 32 and a relatively thick wall 34 having the textured surface 18, a mandrel is dipped four times in the dispersion as described above and the envelope is then cured (still on the mandrel) at about 270° F. for about 90 minutes. Then the four-layer envelope and mandrel is cooled to room temperature and inspected. If the envelope passes inspection, the envelope is partially dipped, such that only about the posterior side of the envelope is submerged in the dispersion. Then the mandrel having the partial fifth layer is permitted to sit at room temperature for about 2.5 minutes to about 5 minutes, whereupon the fifth layer is sprayed with sodium chloride, which embeds itself in the fifth partially stabilized layer. Then the mandrel having the fifth partial layer embedded with sodium chloride is cured at about 270° for about 90 minutes. Then the cured envelope (still on the mandrel) is soaked in water for four to twelve hours or more to dissolve the sodium chloride to remove it from the envelope and expose the texture. Then the envelope is removed from the mandrel and patched. The patch may include a valve for feeding the fill material to the interior of the envelope. Or the valve may be placed at another site on the envelope.

As to applying the textured surface 18 to implant 10 or 36, the following U.S. Patents are hereby incorporated by reference in their entireties: 1) U.S. Pat. No. 5,674,285 issued Oct. 7, 1997 and entitled Mammary Implant Having Shell With Unitary Rough-Textured Outer Layer and 2) U.S. Pat. No. 5,022,942 issued Jun. 11, 1991 and entitled Method Of Making Textured Surface Prosthesis Implants.

As to the fill material 14, preferred fill materials include saline and silicone gel. More preferably, the fill material is a biocompatible responsive gel. As to biocompatible responsive gels, the following U.S. Patent is hereby incorporated by reference in its entirety: U.S. Pat. No. 5,662,708 issued Sep. 2, 1997 and entitled Rheologically Modified And Osmotically Balanced Fill Material For Implant.

Figure 3A:
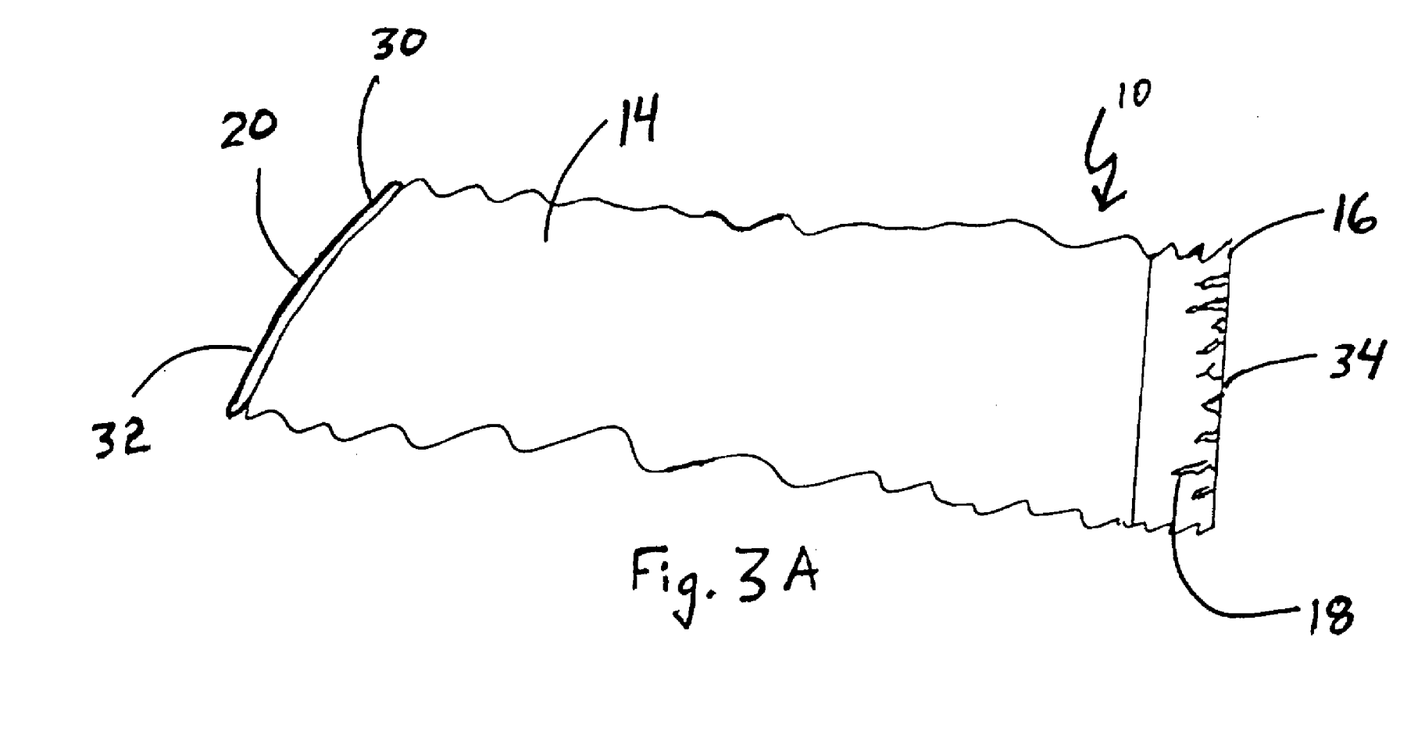
FIG. 3A shows a cross section of the implant of FIG. 1A to show the relatively thin wall of the anterior side of the implant and the relatively thick wall of the posterior side of the implant, and further shows fill material in the implant.
Figure 3B:
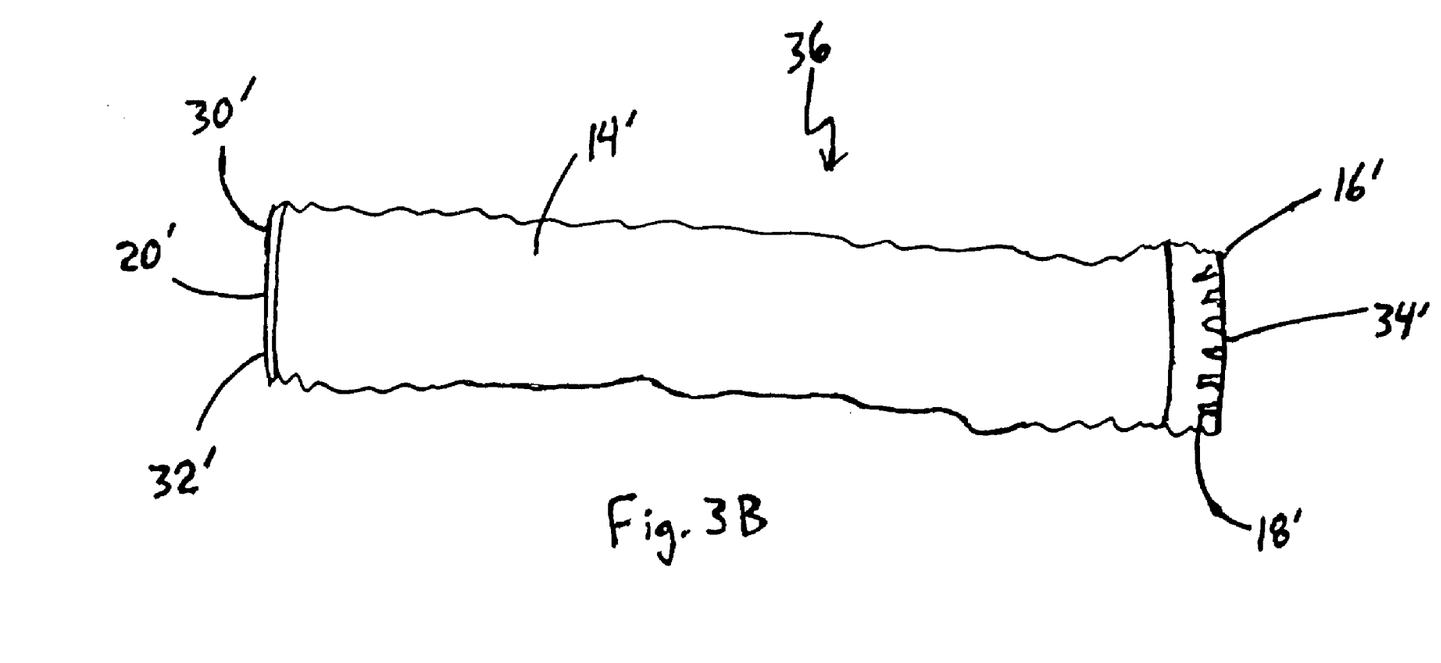
FIG. 3B shows a cross section of the implant of FIG. 2A to show the relatively thin wall of the anterior side of the implant and the relatively thick wall of the posterior side of the implant, and further shows fill material in the implant.

The relative thicknesses of the anterior and posterior walls in FIGS. 3A and 3B are exaggerated for clarity. In practice, anterior wall 32 is preferably between about 12/1000 (0.012) inches thick and about 16/1000 (0.016) inches thick. Posterior wall 34 is preferably between about 14/1000 (0.014) inches thick and about 18/1000 (0.018) inches thick. The posterior wall 34 is preferably about 2/1000 (0.002) inches thicker than the anterior wall 32. Anterior wall 32' is preferably between about 12/1000 (0.012) inches thick and about 16/1000 (0.016) inches thick. Posterior wall 34' is preferably between about 14/1000 (0.014) inches thick and about 18/1000 (0.018) inches thick. The posterior wall 34' is preferably about 2/1000 (0.002) inches thicker than the anterior wall 32'.

The present implants may include room temperature vulcanized (RTV) envelopes. These envelopes are conventionally used with saline fill materials. Saline fill materials tend to be more abrasive, and RTV envelopes resist the abrasiveness of the saline to a better degree than do envelopes that are cured at elevated temperatures. In other words, an RTV envelope may include a textured portion (such as on a posterior portion) and a portion with a smooth surface (such as on an anterior portion).

The present implants are preferably breast implants and, more preferably, anatomical-shaped breast implants. Anatomical-shaped implants have a greater fullness in the inferior pole. Or the anatomical-shaped implant may have a fullness in the inferior pole as shown by implant 70 in FIG. 6A. Here, in FIG. 6A, the roundness or elevation of the implant is shown by phantom lines. The "highest" point on implant 70 is shown by point or nipple region 72 and reference numeral 74 shows a line marking the boundary between the anterior side 76 and the posterior side of implant 70. Loops 78, 80 and 82 mark respective "elevations" between nipple region 72 and boundary line 74 such that the breast implant surface along phantom line 84 has the greatest slope and such that the breast implant surface along phantom line 86 has the least slope. The breast implant surfaces along phantom lines 88 have a progressively lesser slope than the surface along phantom line 84, and these progressively lesser slopes continue between and along surface lines 90, 92, and 94, which lines also radiate from the nipple region 72.

Figure 1A:
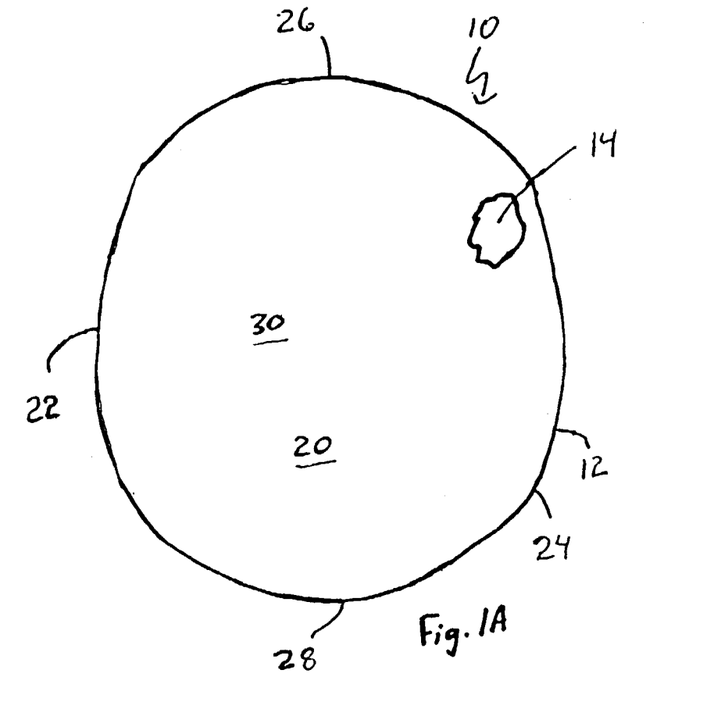
FIG. 1A shows the front side (or anterior side or face) of an anatomical-shaped breast implant.
Figure 1B:
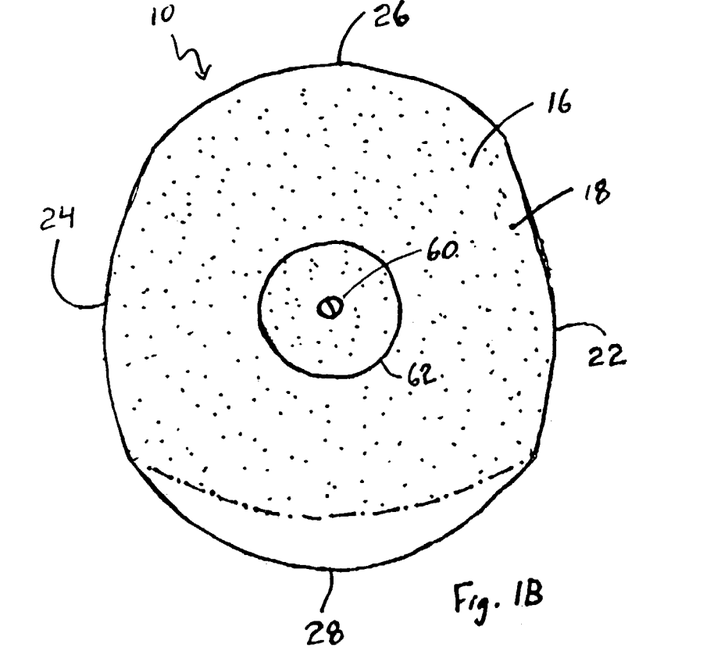
FIG. 1B shows the rear side (or posterior side or face) of the anatomical-shaped breast implant of FIG. 1A.
Figure 1C:
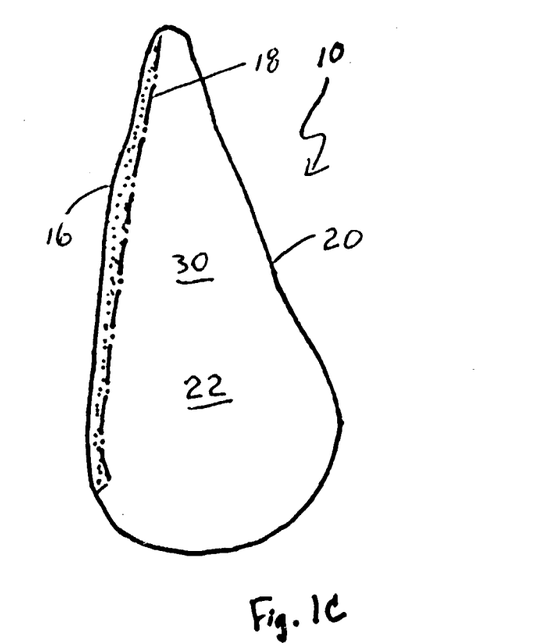
FIG. 1C shows the right side (medial or lateral side dependent upon which breast) of the breast implant of FIG. 1A.
Figure 1D:
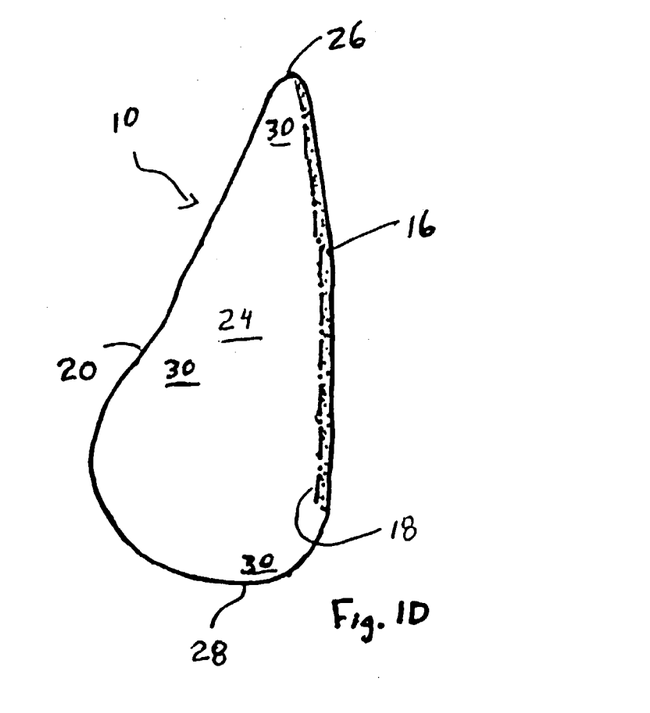
FIG. 1D shows the left side (medial or lateral side dependent upon which breast) of the breast implant of FIG. 1A.
Figure 2A:
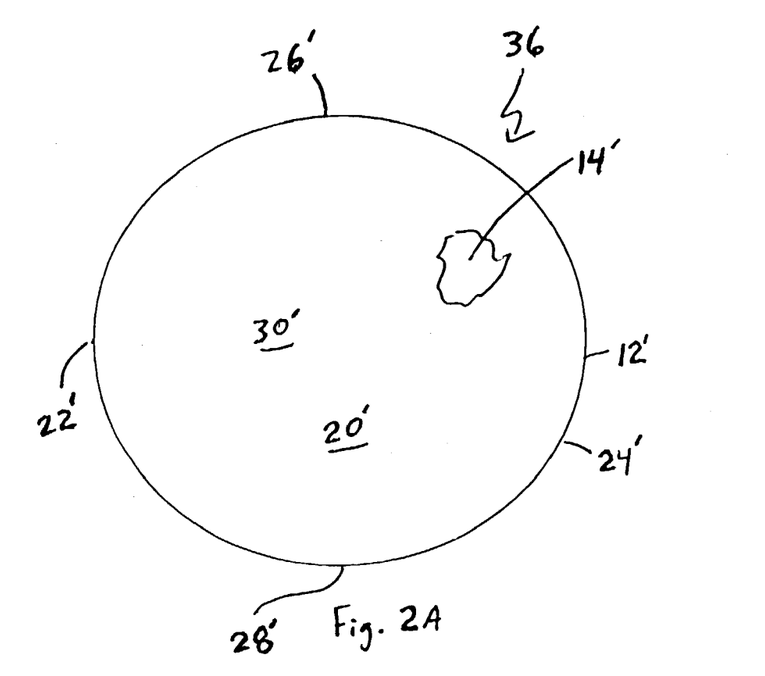
FIG. 2A shows the front side (or anterior side or face) of a round-shaped breast implant.
Figure 2B:
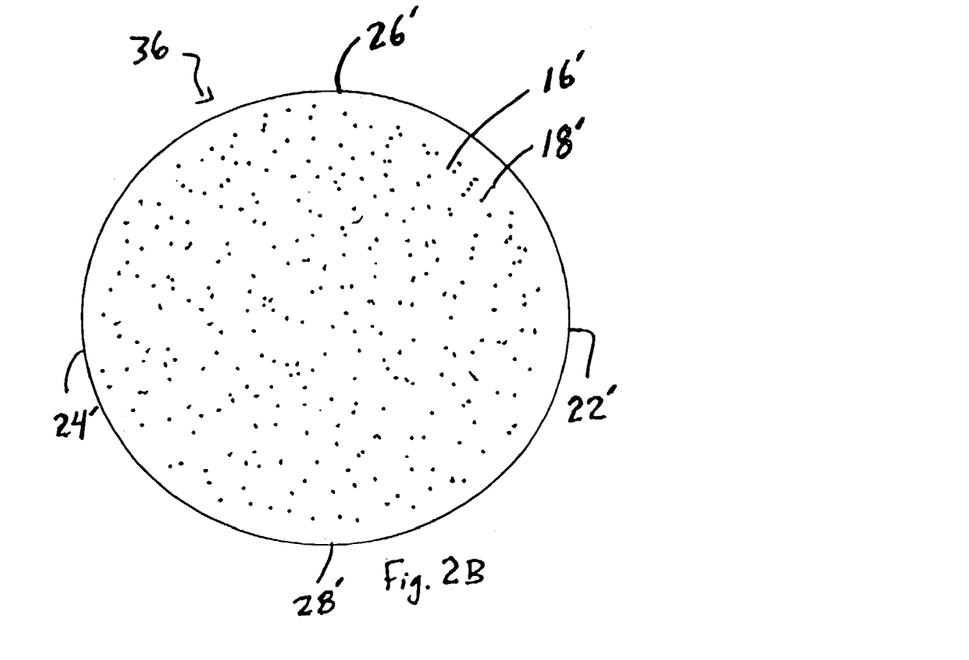
FIG. 2B shows the rear side (or posterior side or face) of the round-shaped breast implant of FIG. 2A.
Figure 2C:
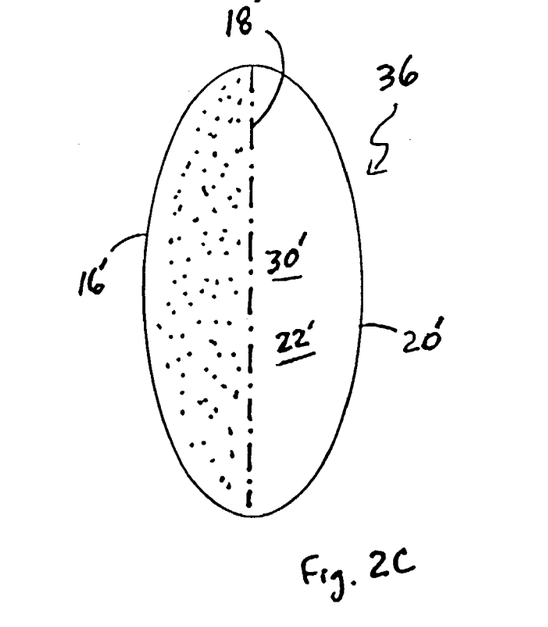
FIG. 2C shows the right side (medial or lateral side dependent upon which breast) of the breast implant of FIG. 2A.
Figure 2D:
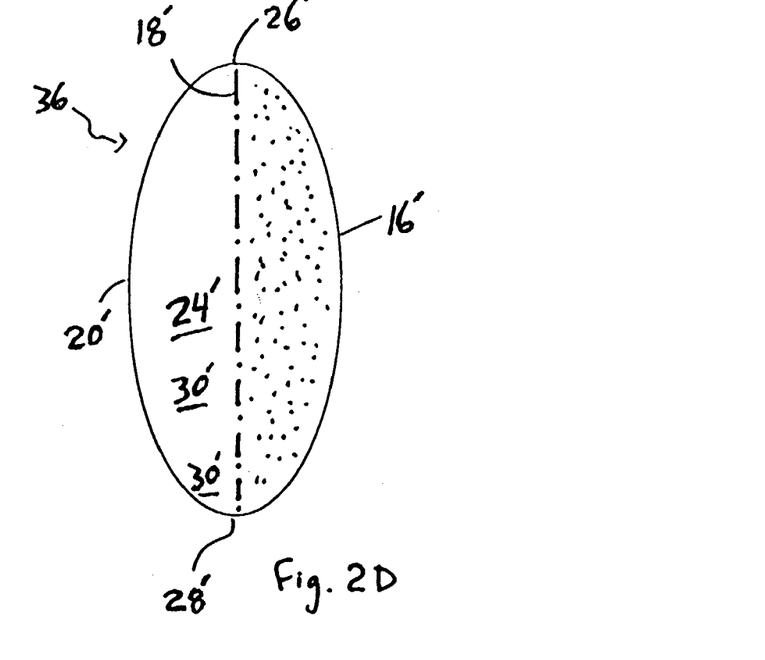
FIG. 2D shows the left side (medial or lateral side dependent upon which breast) of the breast implant of FIG. 2A.

The valve for filling the implant with fill material may be located either posteriorally or anteriorally. A posterior valve 60 is shown in FIG. 1B. The valve 60 may be a leaf valve.

As shown in FIG. 1B, valve 60 is engaged to a patch 62. Patch 62 is a piece of silicone elastomer that is vulcanized to the envelope after the envelope has been removed from the mandrel. In other words, the envelope is first formed by 1) dipping the mandrel four times so as to produce a four layer envelope 2) curing the envelope so that the envelope is vulcanized to a one layer envelope, 3) partially dipping the mandrel and spraying the partial layer with granulate sodium chloride, 4) curing the envelope so that the partial layer is vulcanized to the envelope, 5) and then soaking the envelope to remove the granulate sodium chloride and expose the texture. Then the dipping rod 38, including distal end 49, is removed from the mandrel. A ragged piece of the envelope remains about the area where the distal end 49 had engaged and had been removed from the mandrel. This ragged piece is cut about a line 64, shown in phantom in FIG. 4B. Then the envelope is stretched about the opening left by such cutting such that the mandrel passes through the stretched opening. Then valve 60 is anchored to patch 62. Then patch 62 having valve 60 is vulcanized to the envelope about the opening.

Figure 6B:
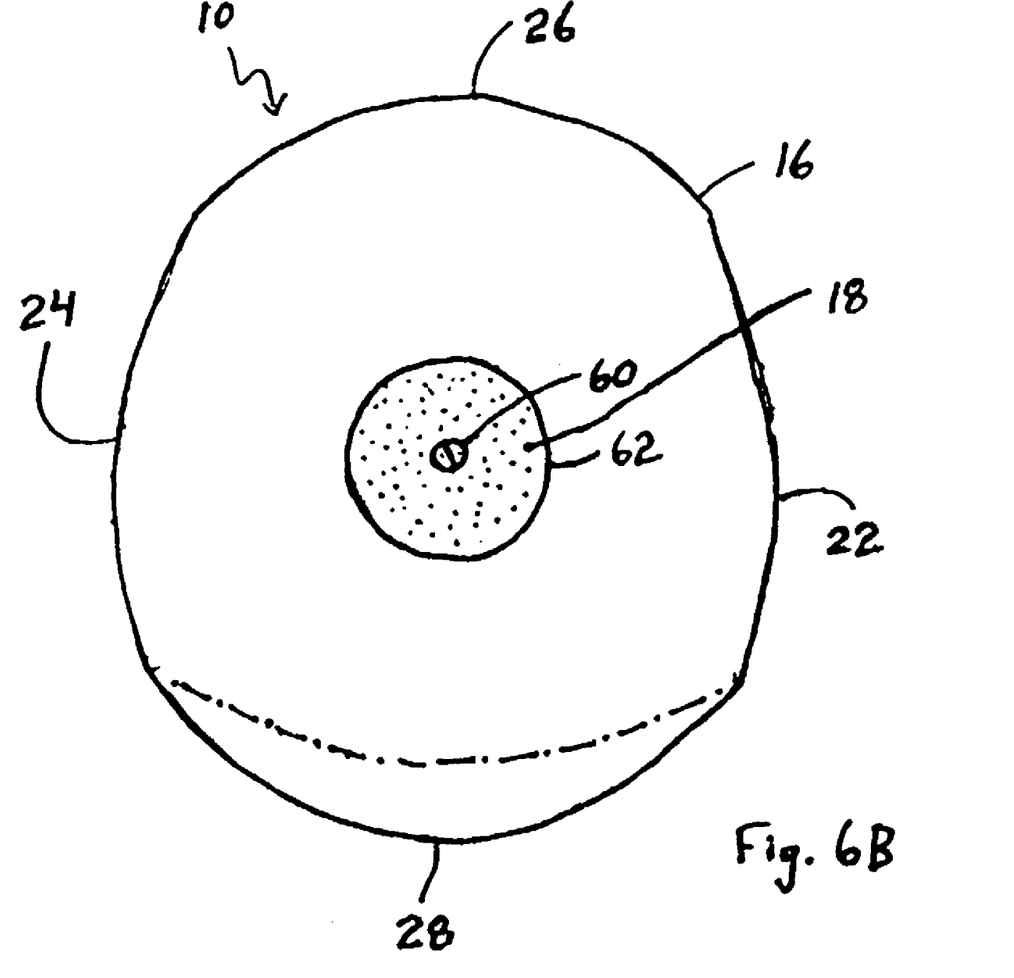
FIG. 6B shows a rear or posterior view of the anatomical-shaped implant of FIGS. 1A–D having only a portion of its surface textured.

The surface of the patch 62 may, if desired, be the only portion of the implant that is textured, as shown in FIG. 6B. The texture 18 of this patch 62 sufficiently interlocks with body tissue to minimize, if not prevent, rotation of implant 10 in the body. Patch 62 has a diameter of about 25% of the diameter of the implant 10.

The area of the surface texture 18 for interlocking with body tissue for anchoring an implant to minimize or even prevent rotation preferably has a surface area of between about 5% and about 50% of the total surface area of the implant, more preferably between about 5% and about 40% of the total surface area of the implant, and most preferably between about 5% and about 30% of the total surface area of the implant. The surface area of the patch 62 is about 5% of the total surface area of the implant 10 shown in FIG. 6B. The surface area of the texture 18' of the round-shaped implant 36 is about 50% of the total surface area of implant 36. The surface area of the texture 18 on the posterior side of implant 10 in FIG. 1B is about 30% of the total surface area of the implant 10 of FIGS. 1A–D.

Preferably, the area of the surface texture 18 is on one side or on less than one side of the implant and covers one portion or block of surface of the implant without breaks in the texturing. However, if desired, the surface texture 18 may form an annular band about the circumference of the implant, or an annular band along less than the circumference of the implant, or a band having two ends along one side of the implant, or a band having two ends along less than one side of the implant. Such bands of texturing may be formed, for example, by placing a template over a partially stabilized but not cured envelope, then spraying the granulate sodium chloride over the template and exposed portion of the partially stabilized but not cured envelope, then removing the template, then curing the envelope, and then soaking the envelope to remove the salt and expose the band of texture.

It should be noted that preferably the textured surface 18 has an aggressive texture and that preferably the smooth surface 30 is perfectly smooth or as perfectly smooth as is practically possible through the process of dipping and curing a silicone elastomer breast envelope. However, if desired, surface 18 may be relatively rough and surface 30 may be relatively smooth. In other words, it should be noted that some texture applied to implant surfaces is very aggressive (has high peaks and low valleys, i.e., the absolute distance between the peaks and valleys is great), that some texture applied to implant surfaces is subtle (has low peaks and high valleys, i.e., the absolute distance between the peaks and valleys is small), and that some texture is not so aggressive and not so subtle.

An aggressive texture performs best for anchoring an implant and such is preferred for a posterior side of a breast implant. On the anterior side of such an implant, a perfectly smooth surface or practically smooth surface is preferred. However, if desired, a less aggressive or subtle texture (i.e. relatively smooth surface) may be used.

As to forming an implant having both an aggressive texture and a less aggressive texture, one side or one portion of the envelope may be sprayed with relatively coarse granules of sodium chloride and the other side or other portion of the envelope may be sprayed with relatively fine particles of sodium chloride. Then the envelope is cured and soaked to remove the salt and expose the texture. The coarse particles produce the relatively aggressive texture. The fine particles produce the relatively subtle texture.

Figure 7A:
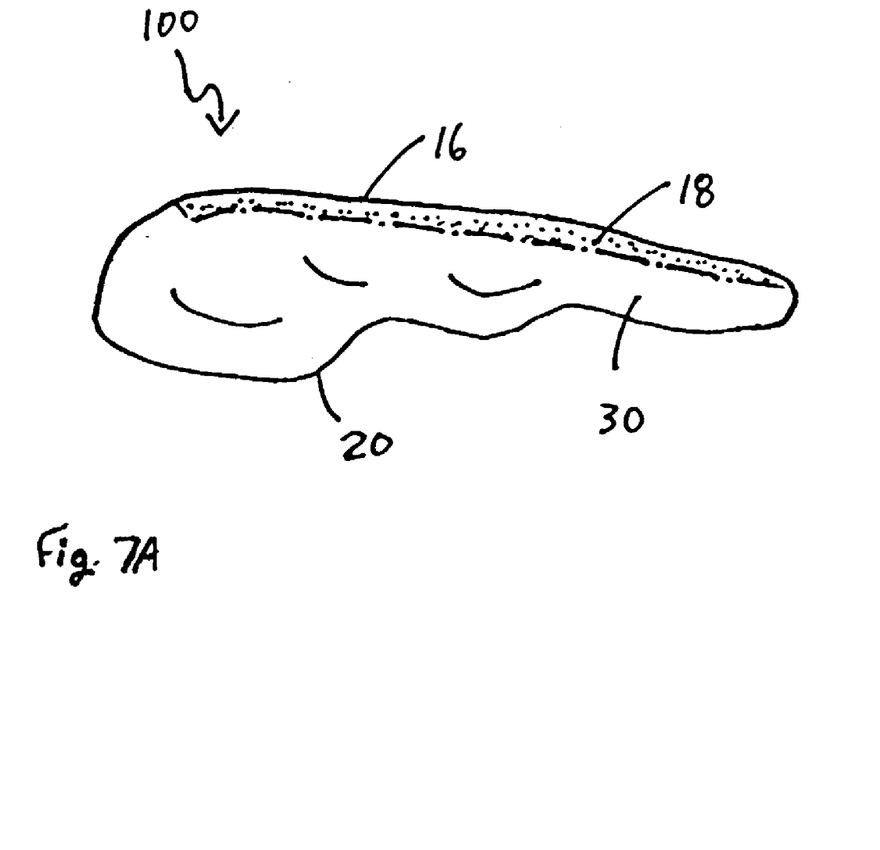
FIG. 7A shows a side view of an inflatable anatomical shaped implant having a textured posterior surface.
Figure 7B:
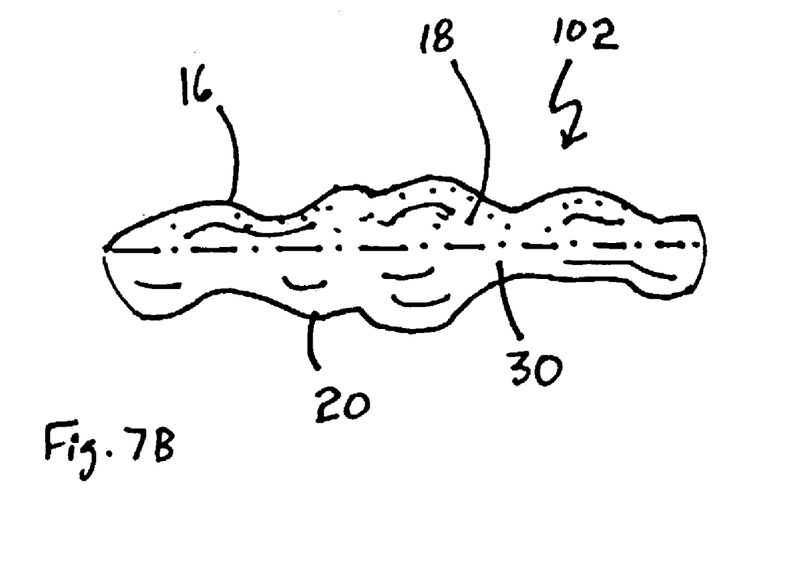
FIG. 7B shows a side view of an inflatable round shaped implant having a textured posterior surface.

The present implants may be inflatable or prefilled implants. In other words, either an inflatable implant or a prefilled implant may include a textured surface portion (such as on a posterior portion) and a portion with a smooth surface (such as on an anterior portion). An inflatable anatomical shaped implant 100 is shown in FIG. 7A having no fill material therein. Implant 100 includes posterior face 16 with texture 18 and an anterior face 20 and smooth surface 30. An inflatable round shaped implant 102 is shown in FIG. 7B having no fill material therein. Implant 102 includes posterior face 16 with texture 18 and an anterior face 20 and smooth surface 30. Implants 100 and 102 are manufactured according to the processes described above. Generally, inflatable implants are surgically implanted into the body and then filled with fill material so as to expand the implant. Prefilled implants are filled at the factory with fill material or filled with fill material prior to being surgically implanted. The implants shown in FIGS. 1A, 1B, 1C, 1D, 2A, 2B, 2C, 2D, 6A and 6B show prefilled implants.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

What is claimed is:

1. A method of making an implant envelope, comprising the steps of:
    a) selecting a mandrel;
    b) selecting a dispersion into which the mandrel is dipped;
    c) fully submerging the mandrel in the dispersion, withdrawing the mandrel from the dispersion and thereby picking up a first envelope layer on the mandrel, and permitting the first envelope layer to at least partially stabilize; and
    d) partially submerging the mandrel in the dispersion, withdrawing the mandrel from the dispersion and thereby picking up a second envelope layer on the mandrel and permitting the second envelope layer to at least partially stabilize, such that a first envelope coating of a first thickness is disposed over one portion of the mandrel and a second an envelope coating of a second thickness is disposed over another portion of the mandrel and wherein the first and second envelope coatings form the implant envelope.

2. The method of claim 1 wherein the step of fully submerging the mandrel occurs prior to the step of partially submerging the mandrel.

3. The method of claim 1 and further comprising:
    e) curing the first envelope layer between the steps of fully submerging the mandrel and partially submerging the mandrel; and
    f) curing the second envelope layer after the step of partially submerging the mandrel.

4. The method of claim 1 wherein the step of partially submerging the mandrel occurs prior to the step of fully submerging the mandrel.

5. The method of claim 1, wherein the implant envelope comprises a breast implant envelope having an anterior side, posterior side, superior pole, inferior pole and a nipple position, with the nipple position being on the anterior side near the inferior pole, wherein the anterior side has a first thickness, wherein the posterior side has a second thickness, wherein the first thickness of the anterior side is less than the second thickness of the posterior side, and wherein the method further comprises the steps of:
    c-1) dipping the mandrel into a fluid to pick up material for only one of the anterior and posterior sides of the envelope; and
    d-1) dipping the mandrel into the fluid to pick up material for the other of the anterior and posterior sides of the envelope.

6. The method of claim 5, and further comprising the steps of:
    c) performing step "c-1") before step "d-1").

7. The method of claim 5, and further comprising the steps of:
    c) performing step "d-1") before step "c-1").

8. A method of claim 1 and further comprising the steps of:
    g) bringing a granulate into contact with a portion of at least one of the at least partially a stabilized envelope layers; then
    h) curing the envelope layer having granulate thereon; and then
    i) removing the granulate to expose texture on the envelope layer.

9. The method of claim 8 wherein a portion of one of the first and second envelope layers is brought into contact with relatively coarse granules and wherein a portion of the other of the first and second envelope layers is brought into contact with relatively fine granules.

* * * * *